(12) United States Patent
Baranski et al.

(10) Patent No.: US 7,642,066 B2
(45) Date of Patent: Jan. 5, 2010

(54) **HIGH THROUGHPUT PHARMACEUTICAL SCREENING USING *DROSOPHILA***

(75) Inventors: Thomas J Baranski, Kirkwood, MO (US); Ross L Cagan, Clayton, MO (US)

(73) Assignee: Washington University, St. Louis, MO (US)

( * ) Notice: Subject to any disclaimer, the term of this patent is extended or adjusted under 35 U.S.C. 154(b) by 158 days.

(21) Appl. No.: 11/036,897

(22) Filed: Jan. 14, 2005

(65) Prior Publication Data

US 2005/0260135 A1 Nov. 24, 2005

Related U.S. Application Data

(60) Provisional application No. 60/536,625, filed on Jan. 15, 2004.

(51) Int. Cl.
*C12Q 1/02* (2006.01)
*A61K 49/00* (2006.01)

(52) U.S. Cl. .......................................... 435/29; 424/9.2

(58) Field of Classification Search ....................... None
See application file for complete search history.

(56) References Cited

U.S. PATENT DOCUMENTS

| | | | |
|---|---|---|---|
| 6,225,120 | B1 | 5/2001 | Ruvukun et al. |
| 6,316,690 | B1 * | 11/2001 | Fogarty ......................... 800/3 |
| 6,506,559 | B1 | 1/2003 | Fire et al. |
| 6,531,644 | B1 | 3/2003 | Duyk et al. |
| 6,548,733 | B2 | 4/2003 | Hafen |
| 2002/0026648 | A1 | 2/2002 | Hafen |
| 2002/0104106 | A1 | 8/2002 | Fogarty |
| 2002/0115129 | A1 | 8/2002 | Sharma et al. |
| 2002/0184656 | A1 | 12/2002 | Bhandari et al. |
| 2003/0033623 | A1 | 2/2003 | Fogarty et al. |
| 2005/0009112 | A1 | 1/2005 | Edgar et al. |
| 2005/0144654 | A1 | 6/2005 | Sharma |
| 2005/0239049 | A1 | 10/2005 | Gunde et al. |
| 2005/0246794 | A1 | 11/2005 | Khvorova et al. |

FOREIGN PATENT DOCUMENTS

| | | |
|---|---|---|
| WO | WO 0078940 A1 * | 12/2000 |
| WO | 01/11076 | 2/2001 |

OTHER PUBLICATIONS

Benkel et al, "A Drosophila gene is subject to glucose repression," (Proc. Natl. Acad. Sci. USA), Genetics, vol. 84, pp. 1337-1339, Mar. 1987.*

Wang et al, "Physiological Genetics of the Response to a High-Sucrose Diet by Drosophila melanogaster," (Biochemical Genetics), vol. 33, Nos. 5/6, 1995, pp. 149-165.*

Acton, D. S., Velthuyzen, D., Lips, C. J., and Hoppener, J. W. (2000). Multiple endocrine neoplasia type 2B mutation in human RET oncogene induces medullary thyroid carcinoma in transgenic mice. Oncogene 19, 3121-3125.

Adachi-Yamada, T., Fujimura-Kamada, K., Nishida, Y. and Matsumoto, K., "Distortion of Proximodistal Information Causes JNK-Dependent Apoptosis in *Drosophila* Wing," Nature, 1999, pp. 166-169, vol. 400.

Alberti, L., Borrello, M. G., Ghizzoni, S., Torriti, F., Rizzetti, M. G., and Pierotti, M. A. (1998). Grb2 binding to the different isoforms of Ret tyrosine kinase. Oncogene 17, 1079-1087.

Arighi, E., Alberti, L., Torriti, F., Ghizzoni, S., Rizzetti, M. G., Pelicci, G., Pasini, B., Bongarzone, I., Piutti, C., Pierotti, M. A., and Borrello, M. G. (1997). Identification of Shc docking site on Ret tyrosine kinase. Oncogene 14, 773-782.

Bardelli, A., Longati, P., Gramaglia, D., Basilico, C., Tamagnone, L., Giordano, S., Ballinari, D., Michieli, P., and Comoglio, P. M. (1998). Uncoupling signal transducers from oncogenic MET mutants abrogates cell transformation and inhibits invasive growth. Proc Natl Acad Sci U S A 95, 14379-14383.

Besset, V., Scott, R. P., and Ibanez, C. F. (2000). Signaling complexes and protein-protein interactions involved in the activation of the Ras and phosphatidylinositol 3-kinase pathways by the c-Ret receptor tyrosine kinase. J Biol Chem 275, 39159-39166.

Bilder, D., Li, M. and Perrimon, N., Cooperative Regulation of Cell Polarity and Growth by *Drosophila* Tumor Suppressors,: Science, 2000, pp. 113-116, vol. 289.

(Continued)

*Primary Examiner*—Jon P Weber
*Assistant Examiner*—Laura Schuberg
(74) *Attorney, Agent, or Firm*—Sonnenschein, Nath & Rosenthal LLP

(57) ABSTRACT

High throughput drug screening assay methods and related apparatus are described. Wild-type *Drosophila* are raised in multi-well microtiter plates on a growth medium having a high level of a sugar such as glucose. The high sugar diet during development induces screenably distinct characteristics in the wild-type *Drosophila*. Compounds that putatively modify the screenably distinct characteristic are tested by feeding to the *Drosophila* embryos, and determining whether the compound modifies the screenably distinct characteristic induced by the high sugar growth medium. The assay methods and related articles of composition can also be used to assay toxicity of candidate compounds.

23 Claims, 4 Drawing Sheets

OTHER PUBLICATIONS

Boa, S. and Cagan, R., "Preferential Adhesion Mediated by Hibris and Roughest Regulates Morphogenesis and Patterning in the Drosophila Eye," Dev. Cell, 2005, pp. 925-935, vol. 8.

Bocciardi, R., Mograbi, B., Pasini, B., Borrello, M. G., Pierotti, M. A., Bourget, I., Fischer, S., Romeo, G., and Rossi, B. (1997). The multiple endocrine neoplasia type 2B point mutation switches the specificity of the Ret tyrosine kinase towards cellular substrates that are susceptible to interact with Crk and Nck. Oncogene 15, 2257-2265.

Bongarzone, I., Vigano, E., Alberti, L., Borrello, M. G., Pasini, B., Greco, A., Mondellini, P., Smith, D. P., Ponder, B. A., Romeo, G., and Pierotti, M. A. (1998). Full activation of MEN2B mutant RET by an additional MEN2A mutation or by ligand GDNF stimulation Oncogene 16, 2295-2301.

Borrello, M. G., Pelicci, G., Arighi, E., De Filippis, L., Greco, A., Bongarzone, I., Rizzetti, M., Pelicci, P. G., and Pierotti, M. A. (1994). The oncogenic versions of the Ret and Trk tyrosine kinases bind Shc and Grb2 adaptor proteins. Oncogene 9, 1661-1668.

Brachmann, C., Jassim, O., Wachsmuth And Cagan, R., "The *Drosophila* Bci-2 Family Member dBorg-1 Functions in the Apoptotic Response to UV=Irradiation," Current Biology, 2000, pp. 547-550, vol. 10.

Brand, A. and A Perrimon, N., "Targeted Gene Expression as a Means of Altering Cell Fates and Generating Dominant Phenotypes," Development, 1993, pp. 401-415, vol. 118.

Brownlee, M., "Biochemistry and Molecular Cell Biology of Diabetic Complications," Nature, 2001, pp. 813-820, vol. 414.

Brumby, A. and Richardson, H., "*Scribble* Mutants Cooperate with Oncogenic Ras or Notch to Cause Neoplastic Overgrowth in *Drosophila*," EMBO J., 2003, 5769-5779, vol. 22.

Califano, D., Rizzo, C., D'Alessio, A., Colucci-D'Amato, G. L., Cali, G., Bartoli, P. C., Santelli, G., Vecchio, G., and De Franciscis, V. (2000). Signaling through Ras is essential for ret oncogene-induced cell differentiation in PC12 cells. J Biol Chem 275, 19297-19305.

Carlomagno, F., Melillo, R. M., Visconti, R., Salvatore, G., De Vita, G., Lupoli, G., Yu, Y., Jing, S., Vecchio, G., Fusco, A., and Santoro, M. (1998). Glial cell line-derived neurotrophic factor differentially stimulates ret mutants associated with the multiple endocrine neoplasia type 2 syndromes and Hirschsprung's disease. Endocrinology 139, 3613-3619.

Carlomagno, F., Vitagliano, D., Guida, T., Ciardiello, F., Tortora, G., Vecchio, G., Ryan, A. J., Fontanini, G., Fusco, A., and Santoro, M. (2002). ZD6474, an orally available inhibitor of KDR tyrosine kinase activity, efficiently blocks oncogenic RET kinases. Cancer Res 62, 7284-7290.

Carlson, K. M., Dou, S., Chi, D., Scavarda, N., Toshima, K., Jackson, C. E., Wells, S. A., Jr., Goodfellow, P. J., and Donis-Keller, H. (1994). Single missense mutation in the tyrosine kinase catalytic domain of the RET protooncogene is associated with multiple endocrine neoplasia type 2B. Proc Natl Acad Sci U S A 91, 1579-1583.

Carlson, K. M., Bracamontes, J., Jackson, C. E., Clark, R., Lacroix, A., Wells, S. A., Jr., and Goodfellow, P. J. (1994). Parent-of-origin effects in multiple endocrine neoplasia type 2B [see comments]. Am J Hum Genet 55, 1076-1082.

Chen, H-2., Chen, X., Oh, S-2, Marinissen, M.K, Gutkind, J. and Hou, S., "Mom identifies a Receptor for the Drosophila JAK/STAT Signal Transduction Pathway and Encodes a Protein Distantly Related to the Mammalian Cytokine Receptor Family," Genes & Development, 2002, pp. 388-398, vol. 16.

Ciardiello, F., Bianco, R., Caputo, R., Damiano, V., Troiani, T., Melisi, D., De Vita, F., De Placido, S., Bianco, A. R., and Tortora, G. (2004). Antitumor activity of ZD6474, a vascular endothelial growth factor receptor tyrosine kinase inhibitor, in human cancer cells with acquired resistance to antiepidermal growth factor receptor therapy. Clin Cancer Res 10, 784-793.

Ciardiello, F., Caputo, R., Damiano, V., Troiani, T., Vitagliano, D., Carlomagno, F., Veneziani, B. M., Fontanini, G., Bianco, A. R., and Tortora, G. (2003). Antitumor effects of ZD6474, a small molecule vascular endothelial growth factor receptor tyrosine kinase inhibitor, with additional activity against epidermal growth factor receptor tyrosine kinase. Clin Cancer Res 9, 1546-1556.

Cirafici, A. M., Salvatore, G., De Vita, G., Carlomagno, F., Dathan, N. A., Visconti, R., Melillo, R. M., Fusco, A., and Santoro, M. (1997). Only the substitution of methionine 918 with a threonine and not with other residues activates RET transforming potential. Endocrinology 138, 1450-1455.

Chung, S. S.M., Ho, E. C.M., Lam, K. S.L., Chung, S. K., "Contribution of Polyol Pathway to Diabetes-Induced Oxidative Stress," J. Am. Soc. Nephrol., 2003, pp. S233-236, vol. 8.

De La Cova, C., Abril, M., Bellosta, P., Gallant, P. and Johnston, L., "*Drosophila* Myc Regulates Organ Size by Inducing Cell Competition," Cell, 2003, pp. 107-116, Vo. 117.

Donis-Keller, H., Dou, S., Chi, D., Carlson, K. M., Toshima, K., Lairmore, T. C., Howe, J.R., Moley, J. F., Goodfellow, P., and Wells, S. A., Jr. (1993). Mutations in the RET proto-oncogene are associated with MEN 2A and FMTC. Hum Mol Genet 2, 851-856.

Durick, K., Gill, G. N., and Taylor, S. S. (1998). Shc and Enigma are both required for mitogenic signaling by Ret/ptc2. Mol Cell Biol 18, 2298-2308.

Eng, C., Mulligan, L. M., Healey, C. S., Houghton, C., Frilling, A., Raue, F., Thomas, G. A., and Ponder, B. A. (1996). Heterogeneous mutation of the RET proto-oncogene in subpopulations of medullary thyroid carcinoma. Cancer Res 56, 2167-2170.

Eng, C., Smith, D. P., Mulligan, L. M., Nagai, M. A., Healey, C. S., Ponder, M. A., Gardner, E., Scheumann, G. F., Jackson, C. E., Tunnacliffe, A., and et al. (1994). Point mutation within the tyrosine kinase domain of the RET proto-oncogene in multiple endocrine neoplasia type 2B and related sporadic tumours [published erratum appears in Hum Mol Genet Apr. 1994 ;3(4):686]. Hum Mol Genet 3, 237-241.

Garcia, R., Bowman, T., Niu, G., Yu, H., Minton, S., Muro-Cacho, C., Cox, C., Falcone, R., Fairclough, Parson, S., Laudano, A., Gazit, A., Levitzki, A., Kraker, A. and Jove, R., "Constitutive Activation of Stat3 by the Src and JAK Tyrosine Kinases participates in Growth Regulation of Human Breast Carcinoma Cells," Oncogene, 2001, pp. 2499-2513, vol. 20.

Glade-Bender, J., Kandel, J. J., and Yamashiro, D. J. (2003). VEGF blocking therapy in the treatment of cancer. Expert Opin Biol Ther 3, 263-276.

Gomez-Skarmeta, J. and Modolell, J., "Araucan and Caupolican Provide a Link Between Compartment Subdivisions and Patterning of Sensory Organs and Veins in the Drosophila Wing," Genes & Development, 1996, p. 2935-2946.

Grimm, S. and Pflugfelder, G., "Control of the Gene Optomotor-Blind in Drosophila Wing Development by *Decapentaplegic* and *Wingless*," Science, 1996, pp. 1601-1604, vol. 271.

Grzeschik, N. and Knust, E., "IrreC/rst-Mediated Cell Sorting During *Drosophila* Pupal Eye Development Depends on Proper Localisation of DE=cadherin," Development, 2005, pp. 2035-2045, vol. 132.

Gumbiner, B., "Regulation of Cadherin-Mediated Adhesion in Morphogenesis," Nature, 2005, pp. 622-634, vol. 6.

Harvey, K., Pfleger, C., and Hariharan, I., "The *Drosophila* Mst Ortholog, *hippo*, Restricts Growth and Cell Proliferation and Promotes Apoptosis," 'Cell, 2003, pp. 457-467, vol. 114.

Hauck, C., Hsia, D., Llic, D., and Schlaepfer, D., "v-Src SH3=Enhanced Interaction with Focal Adhesion Kinase at β Integrin-Containing Invadopodia Promotes Cell Invation," J. Biol. Chem., 2002, p. 12487-12490, vol. 277.

Hayashi, H., Ichihara, M., Iwashita, T., Murakami, H., Shimono, Y., Kawai, K., Kurokawa, K., Murakumo, Y., Imai, T., Funahashi, H., et al. (2000). Characterization of intracellular signals via tyrosine 1062 in RET activated by glial cell line-derived neurotrophic factor. Oncogene 19, 4469-4475.

Hennequin, L. F., Stokes, E. S., Thomas, A. P., Johnstone, C., Ple, P. A., Ogilvie, D. J., Dukes, M., Wedge, S. R., Kendrew, J., and Curwen, J. O. (2002). Novel 4-anilinoquinazolines with C-7 basic side chains: design and structure activity relationship of a series of potent, orally active, VEGF receptor tyrosine kinase inhibitors. J Med Chem 45, 1300-1312.

Hofstra, R. M., Landsvater, R. M., Ceccherini, I., Stulp, R. P., Stelwagen, T., Luo, Y., Pasini, B., Hoppener, J. W., Van Amstel, H. K., Romeo, G., and et al. (1994). A mutation in the RET proto-oncogene associated with multiple endocrine neoplasia type 2B and sporadic medullary thyroid carcinoma [see comments]. Nature 367, 375-376.

Igaki, T., Kanda, H., Yamamoto-Goto, Y., Kanuka, H., Kuranaga, E., Aigaki, T., and Miura, M., "Eiger, A TNF Superfamily Ligand that Triggers the *Drosophila* JNK Pathway," EMBO J., 2002, pp. 3009-3018, vol. 21.

Jassim, O., Fink, J. and Cagan, R., "Dmp53 Protects the *Drosophila* Retina During a Developmentally Regulated DNA Damage Response," EMBO J., 2003, pp. 5622-5632, vol. 22.

Kurokawa, K., Iwashita, T., Murakami, H., Hayashi, H., Kawai, K., and Takahashi, M. (2001). Identification of SNT/FRS2 docking site on RET receptor tyrosine kinase and its role for signal transduction. Oncogene 20, 1929-1938.

Lallier, M., St-Vil, D., Giroux, M., Huot, C., Gaboury, L., Oligny, L., and Desjardins, J. G. (1998). Prophylactic thyroidectomy for medullary thyroid carcinoma in gene carriers of MEN2 syndrome. J Pediatr Surg 33, 846-848.

Lim, L., Manser, E., Leung, T. and Hall, C., "Regulation of Phosphorylation Pathways by p21 GTPases. The p21 Ras-Related Rho Subfamily and its Role in Phosphorylation Signalling Pathways," Eur. J. Biochem., 1996, pp. 171-185, vol. 242.

Lips, C. J., Landsvater, R. M., Hoppener, J. W., Geerdink, R. A., Blijham, G., Van Veen, J. M., Van Gils, A. P., De Wit, M. J., Zewald, R. A., Berends, M. J., and et al. (1994). Clinical screening as compared with DNA analysis in families with multiple endocrine neoplasia type 2A [see comments]. N Engl J Med 331, 828-835.

Liu, X., Vega, Q. C., Decker, R. A., Pandey, A., Worby, C. A., and Dixon, J. E. (1996). Oncogenic RET receptors display different autophosphorylation sites and substrate binding specificities. J Biol Chem 271, 5309-5312.

Marshall, G. M., Peaston, A. E., Hocker, J. E., Smith, S. A., Hansford, L. M., Tobias, V., Norris, M. D., Haber, M., Smith, D. P., Lorenzo, M. J., et al. (1997). Expression of multiple endocrine neoplasia 2B RET in neuroblastoma cells alters cell adhesion in vitro, enhances metastatic behavior in vivo, and activates Jun kinase. Cancer Res 57, 5399-5405.

McEwen, D., and Peifer, M., Puckered, A *Drosophila* MapK Phosphatase, Ensures Cell Viability by Antagonizing JNK=Induced Apoptosis,: Development, 2005, pp. 3935-3946, vol. 132.

Martin-Blanco, E., Gampel A., Ring, J., Virdee, K., Kirov, N., Tolkovsky, A., and Martinez-Arias, A., "Puckered Encodes a Phosphatase That Mediates a Feedback Loop Regulating JNK Activity During Dorsal Closure in *Drosophila*," Genes & Dev., 1998, pp. 557-570, vol. 12.

Melillo, R. M., Carlomagno, F., De Vita, G., Formisano, P., Vecchio, G., Fusco, A., Billaud, M., and Santoro, M. (2001). The insulin receptor substrate (IRS)-1 recruits phosphatidylinositol 3-kinase to Ret: evidence for a competition between Shc and IRS-1 for the binding to Ret. Oncogene 20, 209-218.

Melillo, R. M., Santoro, M., Ong, S. H., Billaud, M., Fusco, A., Hadari, Y. R., Schlessinger, J., and Lax, I. (2001). Docking protein FRS2 links the protein tyrosine kinase RET and its oncogenic forms with the mitogen-activated protein kinase signaling cascade. Mol Cell Biol 21, 4177-4187.

Menko, F. H., Van Der Luijt, R. B., De Valk, I. A., Toorians, A. W., Sepers, J. M., Van Diest, P. J., and Lips, C. J. (2002). Atypical MEN type 2B associated with two germline RET mutations on the same allele not involving codon 918. J Clin Endocrinol Metab 87, 393-397.

Michiels, F. M., Chappuis, S., Caillou, B., Pasini, A., Talbot, M., Monier, R., Lenoir, G. M., Feunteun, J., and Billaud, M. (1997). Development of medullary thyroid carcinoma in transgenic mice expressing the RET protooncogene altered by a multiple endocrine neoplasia type 2A mutation. Proc Natl Acad Sci U S A 94, 3330-3335.

Miller, M., Ginalski, K., Lesyng, B., Nakaigawa, N., Schmidt, L., and Zbar, B. (2001). Structural basis of oncogenic activation caused by point mutations in the kinase domain of the MET proto-oncogene: modeling studies. Proteins 44, 32-43.

Minn, A., Kang, Y., Serganova, I., Gupta, G., Giri, D., Doubrovin, M., Ponomarev, V., Gerald, W., Blasberg, R. and Maaague, J., "Distinct Organ-Specific Metastatic Potential of Individual Breast Cancer Cells and Primary Tumors," J. Clin. Invest., 2005, pp. 44-55, vol. 115.

Moley, J. F., Debenedetti, M. K., Dilley, W. G., Tisell, L. E., and Wells, S. A. (1998). Surgical management of patients with persistent or recurrent medullary thyroid cancer. Journal of Internal Medicine 243, 521-526.

Mora, L., Buettner, R., Seigne, J., Diaz, J., Ahmad, N., Garcia, R., Bowman, T., Falcone, R., Fairclough, R., Cantor, A., Muro-Cacho, C., Livingston, S., Karras, J., Pow-Sang, J., and Jove, R., "Constitution Activation of Stat3 in Human Prostate Tumors and Cell Lines: Direct Inhibition of Stat3 Signaling Induces Apoptosis of Prostate Cancer Cells," Cancer Res., 2002, pp. 6659-6666, vol. 62.

Moreno, E., Basler, K. and Morata, G., "Cells Compete for Decapentaplegic Survival Factor to Prevent Apoptosis in *Drosophila* Wing Development," Nature, 2002, pp. 755-759, vol. 416.

Moses, K., and Rubin, G. M. (1991). Glass encodes a site-specific DNA-binding protein that is regulated in response to positional signals in the developing *Drosophila* eye. Genes Dev 5, 583-593.

Mulligan, L. M., Eng, C., Healey, C. S., Clayton, D., Kwok, J. B., Gardner, E., Ponder, M. A., Frilling, A., Jackson, C. E., Lehnert, H., and et al. (1994). Specific mutations of the RET proto-oncogene are related to disease phenotype in MEN 2A and FMTC. Nat Genet 6, 70-74.

Mulligan, L. M., Kwok, J. B., Healey, C. S., Elsdon, M. J., Eng, C., Gardner, E., Love, D. R., Mole, S. E., Moore, J. K., Papi, L., and et al. (1993). Germ-line mutations of the RET proto-oncogene in multiple endocrine neoplasia type 2A. Nature 363, 458-460.

Myster, S., Cavallo, R., Anderson, C., Fox, D. and Peifer, M., "*Drosophila* p120catenin Plays a Reporting Role in Cell Adhesion But is Not An Essential Adherens Junction Component," J., Cell. Biol., 2003, pp. 433-449, vol. 160.

Neufeld, T., De La Cruz, A., Johnston, L. and Edgar, B., Cell, 1998, pp. 1183-1193, vol. 93. Coordination of Growth and Cell Division in the *Drosophila* Wing.

Ohiwa M., Murakami, H., Iwashita, T., Asai, N., Iwata, Y., Imai, T., Funahashi, H., Takagi, H., and Takahashi, M. (1997). Characterization of Ret-Shc-Grb2 complex induced by GDNF, MEN 2A, and MEN 2B mutations. Biochem Biophys Res Commun 237, 747-751.

Pacquelet, A., Lin, L. And Rorth, P., "Binding Site for p120/o-Catenin is Not Required for *Drosophila* E-Cadherin Function in vivo," J. Cell. Biol., 2003, pp. 313-319, vol. 160.

Page-McCaw, A., Serano, J., Sante, J. and Rubin, G., "*Drosophila* Matrix Metalloproteinases Are Required for Tissue Remodeling, but Not Embryonic Development," Dev. Cell, 2003, pp. 95-106, vol. 4.

Pasini, B., Ceccherini, I., and Romeo, G. (1996). RET mutations in human disease. Trends Genet 12, 138-144.

Pasini, A., Geneste, O., Legrand, P., Schlumberger, M., Rossel, M., Fournier, L., Rudkin, B. B., Schuffenecker, I., Lenoir, G. M., and Billaud, M. (1997). Oncogenic activation of RET by two distinct FMTC mutations affecting the tyrosine kinase domain. Oncogene 15, 393-402.

Pastor-Pareja, J., Grawe, F., Martin-Blanco, E., and Garcia-Bellido, A., "Invasive Cell Behavior During *Drosophila* Imaginal Disc Eversion is Medicated by the JNK Signaling Cascade," Dev. Cell, 2004, pp. 387-399, vol. 7.

Pelicci, G., Troglio, F., Bodini, A., Melillo, R. M., Pettirossi, V., Coda, L., De Giuseppe, A., Santoro, M., and Pelicci, P. G. (2002). The neuron-specific Rai (ShcC) adaptor protein inhibits apoptosis by coupling Ret to the phosphatidylinositol 3-kinase/Akt signaling pathway. Mol Cell Biol 22, 7351-7363.

Perl, A-K., Wilgenbus, P., Dahl, U., Semb, H. and Christofori, G., "A Casual Role for E-Cadherin in the Transition from Adenoma to Carcinoma," Nature, 1998, pp. 190-193, vol. 392.

Pettitt, J., Cox, E., Broadbent, I., Flett, A. and Hardin, J., "The *Caenorhabditis elegans* p120 Catenin Homologue, JAC-1, Modulates Cadherin-Catenin Function During Epdermal Morphogenesis," J., Cell Biol., 2003, pp. 15-22, vol. 162.

Ramet, M., Lanot, R., Zachary, D. and Manfruelli, P., "JNK Signaling Pathway is Required for Efficient Would Healing in *Drosophila*," Dev. Biol., 2002, pp. 145-156, vol. 241.

Reynolds, L., Jones, K., Winton, D. J., Cranston, A., Houghton, C., Howard, L., Ponder, B. A., and Smith, D. P. (2001). C-cell and thyroid epithelial tumours and altered follicular development in transgenic mice expressing the long isoform of MEN 2A RET. Oncogene 20, 3986-3994.

Reynolds, A., Roesel, D., Kanner, S. and Parsons, T., "Transformation-Specific Tyrosine Phosphorylating of a Novel Cellular Protein in Chicken Cells Expressing Oncogenic Variants of the Avian Cellular *src* Gene," Mol. Cell. Biol., 1989, pp. 629-638, vol. 9.

Reynolds, A. and Roczniak-Ferguson, A., "Emerging Roles for p120-Catenin in Cell Adhesion and Cancer," Oncogene, 2004, pp. 7947-7956, vol. 23.

Romeo, G., Ceccherini, I., Celli, J., Priolo, M., Betsos, N., Bonardi, G., Seri, M., Yin, L., Lerone, M., Jasonni, V., and Martucciello, G. (1998). Association of multiple endocrine neoplasia type 2 and Hirschsprung disease. J Intern Med 243, 515-520.

Santoro, M. M., Penengo, L., Minetto, M., Orecchia, S., Cilli, M., and Gaudino, G. (1998). Point mutations in the tyrosine kinase domain release the oncogenic and metastatic potential of the Ron receptor. Oncogene 17, 741-749.

Schuchardt, A., D'Agati, V., Larsson-Blomberg, L., Costantini, F., and Pachnis, V. (1994). Defects in the kidney and enteric nervous system of mice lacking the tyrosine kinase receptor Ret [see comments]. Nature 367, 380-383.

Smith-Hicks, C. L., Sizer, K. C., Powers, J. F., Tischler, A. S., and Costantini, F. (2000). C-cell hyperplasia, pheochromocytoma and sympathoadrenal malformation in a mouse model of multiple endocrine neoplasia type 2B. Embo J 19, 612-622.

Soler, R. M., Dolcet, X., Encinas, M., Egea, J., Bayascas, J. R., and Comella, J. X. (1999). Receptors of the glial cell line-derived neurotrophic factor family of neurotrophic factors signal cell survival through the phosphatidylinositol 3-kinase pathway in spinal cord motoneurons. J Neurosci 19, 9160-9169.

Songyang, Z., Carraway, K., Eck, M., Harrison, S., Feldman, R., Mohammadi, M., Schlessinger, J., Hubbard, S., Smith, D., Eng, C., et al. (1995). Catalytic specificity of protein-tyrosine kinases is critical for selective signalling. Nature 373, 536-539.

Speck, O., Hughes, S., Noren, N., Kullkauskas, R., and Fehon, R., "Moesin Functions Antagonistically to the Rho Pathway to Maintain Epithelial Integrity," Nature, 2003, pp. 83-87, vol. 421.

Speicher, S., Thomas, U., Hinz, U. and Knust, E., "The *Serrate* Locus of *Drosophila* and its Role in Morphogenesis of the Wing Imaginal Discs: Control of Cell Proliferation," Development, 1994, pp. 535-544, vol. 120.

Stronach, B. and Perrimon, N., "Stress Signaling in *Drosophila*," Oncogene, 1999, pp. 6172-6182, vol. 18.

Stowers, R. and Schwartz, T., "A Genetic Method for Generating *Drosophila* Eyes Composed Exclusively of Mitotic Clones of a Single Genotype," Genetics, 1999, pp. 1631-1639, vol. 152.

Stewart, R., Li, D-M, Huang, H. and Xu, T., "A Genetic Screen for Modifiers of the latsTumor Supressor Gene Indeitifies C-Terminatl Src Kinase as a Regulator of Cell Proliferation in *Drosophila*," Oncogene, 2003, pp. 6436-6444, vol. 22.

Takahashi, M., Asai, N., Iwashita, T., Murakami, H., and Ito, S. (1998). Molecular mechanisms of development of multiple endocrine neoplasia 2 by RET mutations. J Intern Med 243, 509-513.

Takahashi, M. (1997). The role of the ret proto-oncogene in human disease. Nagoya J Med Sci 60, 23-30.

Takahashi, M., Ritz, J., and Cooper, G. (1985). Activation of a novel human transforming gene, ret, by DNA rearrangement. Cell 42, 581-588.

Tallini, G. (2002). Molecular pathobiology of thyroid neoplasms. Endocr Pathol 13, 271-288.

Tautz, D., "Hypervariability of Simple Sequences as a General Source for Polymorphic DNA Markers," Nucleic Acids Res., 1989, 6463-6471, vol. 17.

Tsuzuki, T., Takahashi, M., Asai, N., Iwashita, T., Matsuyama, M., and Asai, J. (1995). Spatial and temporal expression of the ret proto-oncogene product in embryonic, infant and adult rat tissues. Oncogene 10, 191-198.

Wedge, S. R., Ogilvie, D. J., Dukes, M., Kendrew, J., Chester, R., Jackson, J. A., Boffey, S. J., Valentine, P. J., Curwen, J. O., Musgrove, H. L., et al. (2002). ZD6474 inhibits vascular endothelial growth factor signaling, angiogenesis, and tumor growth following oral administration. Cancer Res 62, 4645-4655.

Wei, S., Xie, Z., Filenova, E. and Brew, K., "Drosophila TIMP Is a Potent Inhibitor of MMPs and TACE: Similarities in Structure and Function to TIMP-3," Biochem., 2003, pp. 12200-12207, vol. 42.

Wells, S. A. (1994). Genetic tests predict thyroid cancer risk, making preventive surgery possible. Journal of National Cancer Institute 86, 1268-1270.

Bhandari et al., "Studies on Human Colon Cancer Gene *APC* by Targeted Expression in *Drosophila*," Oncogene, 2001, 20:6871-6880.

Mikkers et al., "High-Throughput Retroviral Tagging to Identify Components of Specific Signaling Pathways in Cancer," Nature Genetics, 2002, 32:153-159.

Read et al., "*Drosophila* C-Terminal Src Kinase Negatively Regulates Organ Growth and Cell Proliferation Through Inhibition of the Src, Jun N-Terminal Kinase, and STAT Pathways," Mol. Cell Biol, 2004, 24:6676-6689.

Tarunina et al., "Functional Genetic Screens for Genes Involved in Senescence: Role of Tid1, a Homologue of the *Drosophila* Tumor Suppresor *l(2)tid*, in Senescence and Cell Survival," Mol Cell Biol., 2004, 24:10792-10801.

Willingham et al., "RNAi and HTS: Exploring Cancer by Systemic Loss of Function," Oncogene, 2004, 24:8392-8400.

Daneman et al., "The Blood-Brain Barrier-Lessons from Moody Files," Cell, 2004, 123:9-12.

Ichihara et al., "RET and Neuroendocrine Tumors," Cancer Lett., 2004, 203:197-211.

Pedraza et al., *Drosophila* Src-Family Kinases Function with Csk to Regulate Cell Prliferation and Apoptosis,: Oncogene, 2003, 23:4754-4762.

Read et al., "a *Drosophila* Model of Multiple Endocrine Neoplasia Type 2," Genetics, 2005; 171:1057-1081.

Vidal et al., "ZD6474 Suppresses Oncogenic RET isoforms in a *Drosophila* Model for Type 2 Multiple Endocrine Neoplasia Syndromes and Papillary Thyroid Carcinoma," Cancer Res., 2004, 65:3538-3541.

Vidal et al., "Drosophila Models for Cancer Research," Curr. Opin. Genet. Dev., 2006, 16:10-16.

Wimmer, "Innovations: Applications of Insect Transgenesis," Nat. Rev. Genet., 2003, 4:225-232.

Yeo, "Splicing Regulators" Targets and Drugs, Gennome Biol., 2005, 6:240.

Brownlee, "Biochemistry and Molecular Cell Biology of Diabetic Complications," Nature, 2001, pp. 813-820, vol. 414.

Chung et al., "Contribution of Polyol Pathway to Diabetes-Induced Oxidative Stress," J. Am. Soc. Nephrol., 2003, pp. S233-236, vol. 8.

Evans et al., "Oxidative Stress and Stress-Activated Signaling Pathways: A Unifying Hypothesis of Type 2 Diabetes," Endocr. Rev., 2002, pp. 599-622, vol. 23.

Garofalo, "Genetic Analysis of Insulin Signaling in *Dropophila*," Trends in Endocrin. Metabol., 2002, pp. 156-162.

McMillan et al., "The Homeotic Gene *spineless-aristapedia* Affects Geotaxis in *Drosophila melanogaster*," Behav. Genet., 1992, pp. 557-573, vol. 22.

Rulifson et al., "Ablation of Insulin-Producing Neurons in Flies: Growth and Diabetic Phenotypes," Science, 2002, pp. 1118-1120, vol. 296.

Rumberger et al., "Role of Hexosamine Biosynthesis in Glucose-Mediated Up-Regulation of Lipogenic Enzyme mRNA Levels: Effects of Glucose, Glutamine, and Glucosamine on Glycerophosphate Dehydrogenase, Fatty Acid Synthase, and Acetyl-CoA Carboxylase mRNA Levels," J. Biol. Chem., 2003, pp. 28547-28552, vol. 278.

Toma et al., "Identification of Genes Involved in *Drosophila melanogaster* Geotaxis, a Complex Behavioral Trait," Nature Genetics, 2002, pp. 349-353, vol. 31.

Tomlinson et al., "Aldose Reductase Inhibitors and Their Potential for the Treatment of Diabetic Complications," Trends Pharmacol. Sci., 1994, pp. 293-297, vol. 15.

Wells et al., "A Role for N-Acetylglucosamine as a Nutrient Sensor and Mediator of Insulin Resistance," Cell Mol. Life Sci., 2003, pp. 222-228, vol. 60.

Wells et al., "O-GIcNAc Tums Twenty: Functional Implications for Post-Translational Modification of Nuclear and Cytosolic Proteins with a Sugar," FEBS Lett., 2003, pp. 154-158, vol. 546.

Yasuda et al., "Diabetic Neuropathy and Nerve Regeneration," Prog. Neurobiol., 2001, pp. 229-285, vol. 69.

Supplemental European Search Report issued on Jul. 16, 2009 in connection with related EP Patent Application No. 05705734.1.

Kang, Soon-Ja et al., Effect of dietary carbohydrates on the expression of GPDH isozymes in *Drosophila melanogaster*, Korean Journal of Genetics 1999 pp. 19-28, vol. 21 No. 1.

Zinke, Ingo et al., Nutrient control of gene expression in Drosophila: microarray analysis of starvation and sugar-dependant response, The EMBO Journal 2002 pp. 6162-6173, vol. 21 No. 22.

Tanimura, T. et al., Genetic dimorphism in the taste sensitivity to trehalose in drosophilia-melanogaster, Journal of Comparative Physiology A sensory Neural and Behavioral Physiology 1982 pp. 433-438, vol. 147 No. 4.

Lynch, D. W. et al., Evaluation of *drosophila* for screening developmental toxicants: test results with eighteen chemicals and presentation of a *drosophila* bioassy, Teratogenesis, Carcinogenesis, Mutagenesis, 1991 pp. 147-173, vol. 11 No. 3.

Turco, F. et al., Strain-induced in incorporation coefficient variation in the growth of $Al_{1-x}In_x$ as alloys by molecular beam epitaxy, Applied Physics Letters 1987 pp. 1989-1991 vol. 51 No. 24.

* cited by examiner

HIGH THROUGHPUT PHARMACEUTICAL SCREENING USING *DROSOPHILA*

CROSS-REFERENCE TO RELATED APPLICATIONS

This application claims the benefit of prior U.S. provisional application Ser. No. 60/536,625, filed Jan. 15, 2004, the specification of which is herein incorporated by reference in its entirety.

STATEMENT REGARDING FEDERALLY SPONSORED RESEARCH OR DEVELOPMENT

Not applicable.

BACKGROUND OF THE INVENTION

The present invention relates in general to the field of drug assaying techniques, and in particular to a novel high throughput screening assay for screening libraries of candidate compounds.

Recent scientific and technological advances have introduced new opportunities and challenges for drug discovery research. The increased availability of chemical libraries, including peptide and oligonucleotide libraries, and robotic systems enable virtually simultaneous synthesis and testing of hundreds or thousands of compounds. However, while screening of large numbers of candidate compounds is a critical early step in drug discovery and development, it can also be a bottleneck.

High throughput screening (HTS) assays and techniques of various types are typically used to screen chemical libraries consisting of large numbers of small molecules for their ability to suppress or enhance disease processes. Cell-free assays provide, for example, identification of putative drug targets implicated in a specific disease condition, such as a specific enzymatic reaction. Cell-based assays, for example, can provide insights into mechanisms underlying disease pathogenesis, and can also provide information on possible toxicity of candidate compounds. In either case, the goal of such screening is to identify the most likely candidates or "lead compounds" for use in further drug discovery and developments efforts, and not to identify a specific drug. The strength of a particular screening technique lies substantially in its ability to rapidly and efficiently screen large libraries of compounds while remaining cost effective.

Automated HTS assays and techniques and robotic systems for drug discovery have been described. The ability to perform a wide variety of biochemical and molecular biology tests using automated systems is widely known, including the ability to perform tests based using enzymatic activity, ELISA, receptor binding, macromolecular interactions, protein expression, and protein folding and assembly. Screens are typically carried out using multi-well microtiter plates. In drug discovery, a typical example of high throughput capacity is about one hundred to a few hundred plates per week depending on desired number of data points, the time required for all underlying biochemical reactions to occur, and the relative complexity of the scoring system used to determine whether a compound has an effect. A premium therefore exists on methods that simplify and speed detection of assay results.

A small molecular weight compound high throughput screening system using genetically modified *Drosophila melanogaster* has been described. U.S. Pub. No.: US 2002/0026648 A1. Compounds of interest are microinjected into the open hemolymph of genetically manipulated *Drosophila* that have been modified with mutations within a selected signaling pathway of interest. However, suitably genetically modified *Drosophila* are limited in availability and are often costly or difficult to obtain. Further, microinjection of compounds of interest into numerous *Drosophila* is technically difficult, and is particularly so in a high throughput context where the ability to automate is especially important. In addition, delivery of candidate compounds by microinjection occurs more slowly and can miss orally absorbable drugs.

Accordingly, there remains a need for methods and related articles of manufacture that improve the ability to screen through chemical libraries consisting of large numbers of candidate compounds to rapidly and easily identify the most likely candidate compounds for further drug discovery and research efforts.

BRIEF SUMMARY CF THE INVENTION

The present invention is based in part on the surprising discovery that screenably distinct characteristics can be induced in wild-type *Drosophila*. These characteristics are useful in high throughput screening because candidate compounds may have the ability to modify expression of these characteristics. In an exemplary embodiment, certain screenably distinct characteristics are produced when a high glucose diet is fed to wild-type *Drosophila* embryos. The same effect is produced by other sugars including other hexose sugars that are products of glucose, including fructose, sorbitol, galactose, glucosamine, as well as by complex sugars such as sucrose. The methods and related articles of manufacture are easily practiced, avoid the need for complex microinjection systems, identify orally absorbable drugs, and are readily adapted to automated high throughput systems.

Accordingly, in one embodiment there is provided a method for high throughput screening of compounds including inducing a screenably distinct characteristic in wild-type *Drosophila* by feeding a high sugar diet to *Drosophila* embryos, feeding to the *Drosophila* embryos a compound that putatively modifies the screenably distinct characteristic, and screening the *Drosophila* to determine whether the compound modifies the screenably distinct characteristic. In exemplary embodiments, the sugar is a hexose sugar, such as glucose. The screenably distinct characteristic is, for example, ataxia, or developmental arrest of *Drosophila*. Alternatively, the screenably distinct characteristic comprises an effect of neuropathy. The screenably distinct characteristic can also be an effect of glucose toxicity. In another embodiment, the method further includes screening the *Drosophila* to determine whether the compound has a toxic effect on the *Drosophila*.

In another embodiment, there is provided a method of using wild-type *Drosophila* in a high throughput screening assay of compounds putatively modifying a screenably distinct characteristic in the wild-type *Drosophila*, the method comprising plating at least one wild-type *Drosophila* embryo in each of multiple wells in a multi-well microtiter plate, inducing the screenably distinct characteristic in a plurality of the wild-type *Drosophila* embryos by feeding a high sugar diet to the *Drosophila* embryos, and screening the *Drosophila* to determine whether a candidate compound modifies the induced screenably distinct characteristic. In exemplary embodiments, the sugar is glucose. The screenably distinct characteristic is, for example, ataxia, or developmental arrest of *Drosophila*. Alternatively, the screenably distinct characteristic comprises an effect of neuropathy. The screenably distinct characteristic can also be an effect of glucose toxicity.

In another embodiment, the method further includes screening the Drosophila to determine whether the compound has a toxic effect on the Drosophila.

In another embodiment, there is provided a method of preparing wild-type Drosophila for use in a high throughput screening assay method, said method comprising feeding a high sugar diet to wild-type Drosophila embryos thereby inducing a screenably distinct characteristic in the wild-type Drosophila. In exemplary embodiments, the sugar is glucose. The screenably distinct characteristic is, for example, developmental arrest or ataxia.

In another embodiment, there is provided an apparatus for use in a high throughput screening assay method, the apparatus including a multi-well microtiter plate, an amount of a high sugar Drosophila growth medium placed into multiple wells of said multi-well microtiter plate, an amount of a candidate compound added to said multiple wells, and a plurality of screenably distinct wild-type Drosophila in said multiple wells, the screenably distinct Drosophila having developed from wild-type Drosophila embryos fed the high sugar growth medium. In exemplary embodiments, the sugar is glucose. The screenably distinct Drosophila include, for example, developmentally arrested Drosophila embryos or ataxic Drosophila. In one embodiment, the apparatus further includes a sealing film for sealing each well of the multi-well microtiter plate. The sealing film is, for example, Aeraseal sealing film.

In another embodiment there is provided a kit for use in a method for high throughput screening of compounds, the kit including instructions including the following: instructions for inducing a screenably distinct characteristic in wild-type Drosophila by feeding a high hexose sugar diet to the wild-type Drosophila embryos, instructions for feeding to the Drosophila embryos a compound that putatively modifies the screenably distinct characteristic, and instructions for screening the Drosophila to determine whether the compound modifies the screenably distinct characteristic. In exemplary embodiments, the high sugar diet is a high glucose diet In one embodiment, the instructions set forth instructions for inducing developmental arrest of Drosophila embryos. In another embodiment, the instructions set forth instructions for inducing ataxia in the Drosophila. In another embodiment, the instructions set forth instructions for inducing neuropathy in the Drosophila. In another embodiment, the instructions set forth instructions for screening the Drosophila to determine whether the compound modifies glucose-mediated toxicity in the Drosophila. In still another embodiment, the instructions set forth instructions for determining whether the compound has a toxic effect on the Drosophila. In yet another embodiment, the kit further includes a multi-well microtiter plate, and an amount of a high sugar Drosophila growth medium for placement into multiple wells of said multi-well microtiter plate. The kit can still further include a sealing film for sealing each well of the multi-well microtiter plate, and an exemplary sealing film is Aeraseal sealing film.

These and other features, aspects and advantages of the present invention will become better understood with reference to the following description, examples and appended claims.

DETAILED DESCRIPTION OF THE INVENTION

Abbreviations and Definitions

Figure 1:
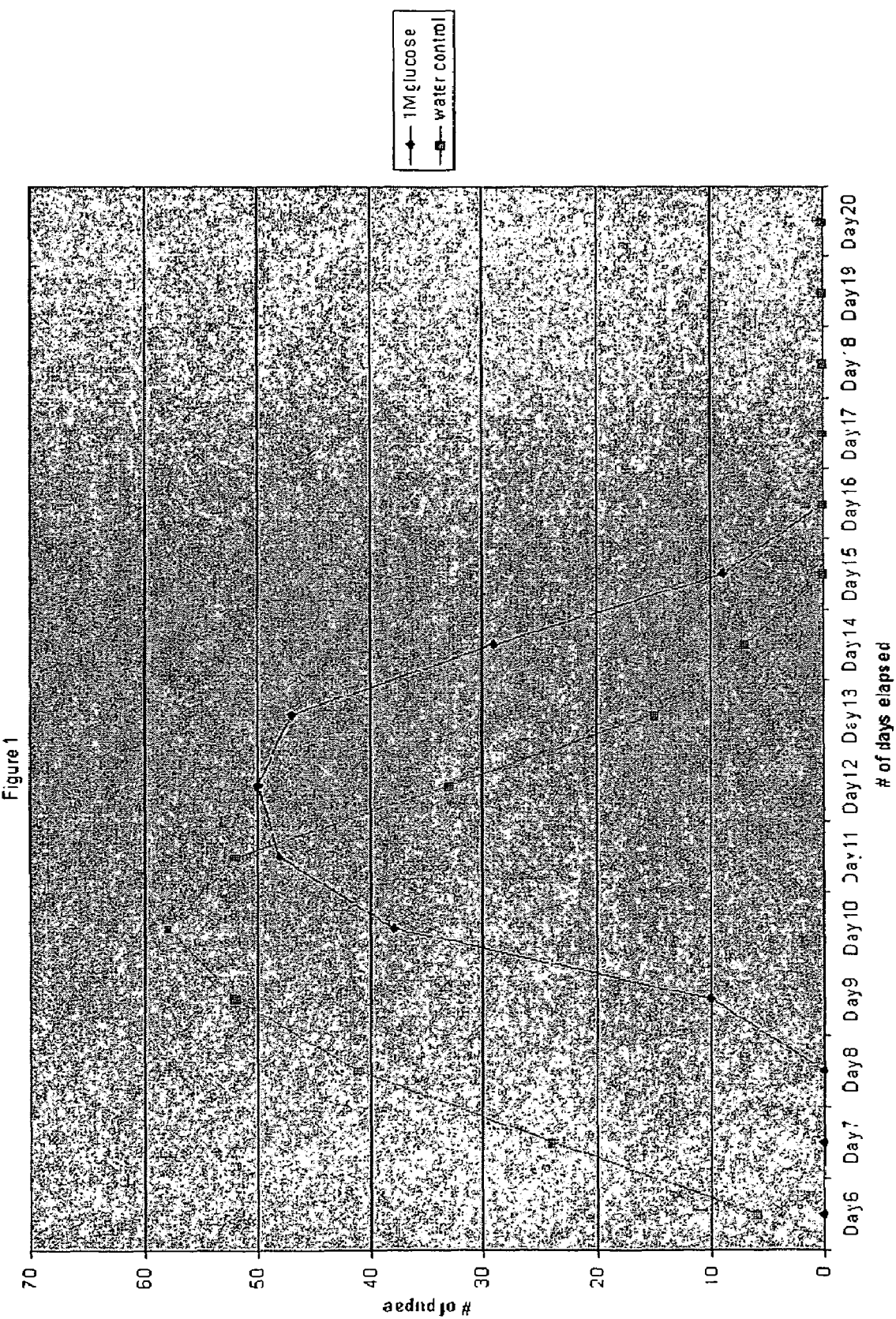
FIG. 1 is a graph showing a delaying effect of a high glucose growth medium on pupariation.

Unless indicated otherwise, the terms defined below have the following meanings:

As used herein, "Drosophila" refers to an insect or insects belonging to the fruit fly species Drosophila melanogaster, without regard to developmental stage thereof and including embryos (eggs), larvae, pupae and mature adult flies of the species.

As used herein, "wild type" refers to Drosophila having a genome that has not been genetically modified or manipulated in a laboratory, for example by recombinant techniques.

As used herein, "to screen" refers to the act of examining a group of organisms, such as Drosophila, and using the expression of a selected characteristic as a criterion for separating the organisms into at least two groups.

As used herein, the term "screenably distinct" refers to a characteristic of a Drosophila individual or individuals, or to the Drosophila individual per se, that deviates from the standard form of wild type individual Drosophila in such as way that visual inspection or other simple detection methods can be used to detect the presence of the characteristic, wherein the presence or absence of the characteristic is used as the criterion for screening the organisms into at least two groups. A screenably distinct characteristic may be a feature of a phenotypic variant of wild-type Drosophila in the sense that the characteristic may result from an interaction of the wild type Drosophila genome with the environment.

As used herein, the term "variant" refers to a Drosophila individual that deviates from the standard form of wild type individual Drosophila with respect to at least one characteristic.

As used herein, "ataxia" refers to a relative inability of an affected organism to coordinate voluntary muscular activity to produce coordinated movement, as compared to an unaffected organism.

As used herein, "developmental arrest" refers to a relative delay in progress of an affected organism through an expected stereotyped schedule of cellular growth and differentiation that leads, for example in the case of Drosophila, from egg to larva, pupa and finally to adult fly.

As used herein, "embryo" and "embryos" refer to the egg stage of Drosophila melanogaster.

As used herein, "toxic" and "toxicity" refer to a characteristic of a compound that through its chemical action kills, injures or impairs an organism. In the present context, high levels of glucose are toxic in Drosophila by prolonging larval development by greater than or equal to 48 hours relative to larvae grown on standard medium. It is expected that some certain candidate compounds subject to the screening methods will be toxic to Drosophila in other detectable ways.

As used herein, "hexose sugar" refers to hexose sugars and hexose products of glucose metabolism, including glucose, fructose, sorbitol, galactose, and glucosamine.

As used herein "sugar" broadly encompasses hexose sugars, as well as complex sugars such as sucrose, lactose and maltose.

As used herein, "high sugar" refers to a characteristic of a Drosophila growth medium including an added amount of a hexose sugar or a complex sugar such as sucrose, lactose or maltose. A high sugar growth medium is therefore any growth medium including an amount of one or more sugars in excess of the total amount of sugars normally present in the growth medium. The total amount of sugars normally present, and therefore an amount which is in excess, varies with the sugar or sugars selected.

As used herein, "high hexose" refers to a characteristic of a Drosophila growth medium including an added amount of a hexose sugar. The amount qualifying as "high hexose" varies with the hexose sugar selected. A high hexose growth medium using any one of glucose (see also the definition for "high glucose", infra), fructose and sorbitol includes the hexose in the range of about 0.5 to about 1.0 molar in excess of the hexose sugars normally present in the growth medium. A high hexose growth medium using galactose includes galactose at a final concentration of about 0.3 M in the growth medium. A high hexose growth medium using glucosamine includes glucosamine at a final concentration of about 3 mM in the growth medium.

As used herein with respect a Drosophila growth medium, "high glucose" refers to a characteristic of a Drosophila growth medium including an amount of glucose in the range of about 1.2 to about 1.8 molar final concentration in the growth media. While standard growth media typically include some amount of glucose and/or molasses, the range of about 1.2 to about 1.8 molar glucose final concentration is higher than that of standard growth media.

As used herein, "to plate" refers to the act of placing material into wells of a microtiter plate, including growth medium, candidate compounds, and Drosophila embryos.

The methods and related articles of composition of the present invention are based in part on the novel combined use of a high glucose Drosophila growth medium and wild type Drosophila to produce screenable phenotypes. Surprisingly, a high glucose diet fed to Drosophila during development produces developmental arrest in developing Drosophila, and ataxia in mature Drosophila. The ataxia is believed b be the result of glucose toxicity manifesting as neuropathy during development of the fly larvae. While the precise nature of the mechanisms underlying the glucose-induced ataxia are unknown, different hexose sugars make the ataxia more severe, implicating glucose metabolites.

Accordingly, methods and related articles of composition for high throughput screening assays involve the preparation of microtiter plates each with multiple wells, wherein each well initially contains one or more wild type Drosophila embryos and an amount of a high glucose Drosophila growth medium. The embryos develop while feeding on the high glucose growth medium. The precise age of the embryos at the time they are plated matters less than the fact that they are all about the same age, to permit accurate evaluation of the possible effects of the candidate compound on larval development.

To prepare the microtiter plates, for example, 96-well microtiter plates are used, such as those commonly commercially available and typically used for various laboratory assay techniques, including other high throughput drug assay techniques. A suitable example is a Falcon #3912 flexible 96-well plate. However, other multiple-well microtiter plates can be used.

Into each well is pipetted 50-400 µl of either standard (control) or high glucose (experimental) Drosophila growth medium. A range of 50-400 µl is a balance between (1) providing sufficient food so as not to place undue feeding stress on the developing flies and (2) providing sufficient air space for the third larval instars to find sufficient wall space to pupate. Any one of several standard Drosophila growth medium recipes as known in the art of breeding Drosophila for research can be used. A known recipe for a standard growth medium includes, for example, water: 1 liter, corn-meal: 61 grams, yeast: 32 grams, agar: 9.3 grams, glucose: 129 grams (or molasses: 67 grams), methyl p-hydrobenzoate: 2.7 grams, and propionic acid: 0.05 liters. A high glucose growth medium is, for example, such a standard Drosophila growth medium supplemented with an additional 1 mole glucose. For example, to prepare a high glucose growth medium, an additional 180 grams of glucose is added to the recipe for standard growth medium as just described. Another embodiment, for example, of a standard growth medium is that prepared as follows: 1 gram agar, 8 grams brewers yeast, 2 grams yeast extract, 2 grams peptone, 3 grams sucrose, 6 grams glucose, 0.05 grams $MgSO_4 \times 6H_2O$, 0.05 grams $CaCl_2 \times 2H_2O$, 600 microliters propionic acid, 1 milliliter 10% p-Hydroxy-benzoic acid methyl ester in 95% ethanol, brought to 100 milliliters with water. A high glucose version of this medium is made, for example, by combining 75 milliliters of this medium with 25 milliliters of a 4 molar glucose solution in water.

Alternatively, the experimental growth medium is any growth medium containing an excess amount of a sugar or sugars selected from hexose sugars such as fructose, sorbitol, galactose and glucosamine, and from complex sugars such as sucrose, lactose or maltose.

FIG. 1 compares effects of standard growth medium and high glucose growth medium, and demonstrates a typical effect of a high glucose growth medium on pupariation: the control (no additional glucose added to the standard Drosophila growth media) began significant levels of pupariation at day 7-8, reaching high levels of eclosion at day 9. The addition of 1 molar (1 M) glucose to the Drosophila growth media delayed pupariation, which reached significant levels at day 10 and high levels at day 11.

A candidate compound, or cocktail of more than one compound, that has been selected for screening is dissolved in EtOH or prepared in DMSO/Aqueous solution. In an exemplary embodiment, EtOH is used. Although DMSO can be used, it can be toxic if it reaches final concentrations of more than 0.3% of the growth medium. The compound in solution is added and allowed to diffuse through the growth medium for an initial period of about 16-24 hours. Wild type Drosophila embryos are collected en masse and, after the initial period of diffusion of the candidate compound through the growth medium, sorted several to a well. In an exemplary embodiment, five to twenty embryos are sorted to each well. However, the number of embryos in each well can easily vary, provided that no more embryos than will flourish in the well are used. The number of embryos per well will also be influenced by the need to obtain a sufficient number of data points to make the test meaningful.

Once the Drosophila embryos are placed into each well on the growth medium, they hatch out and begin feeding after a second period of about 24 hours, bringing the final amount of diffusion time for the subject compound to about 40-48 hours. A period of about 24-48 hours is sufficient for full diffusion of most compounds. In some cases where adequate diffusion of the compound does not occur within a period of about 48 hours, the growth medium in the plate can be warmed and then sonicated to facilitate mixing of the candidate compound with the growth medium. Finally, each well is sealed with a sealing film such as "Aeraseal Sealing Film" (available from Sigma-Aldrich, St. Louis, Mo.; Sigma #A-9224). While other sealing films may be used, exemplary sealing films will not involve the use of potentially toxic components, such as adhesives for sealing, or solvents for applying adhesives to the film, that will harm the developing *Drosophila*. Exemplary sealing films will have a pore size sufficiently small to prevent the escape of young larvae, and also will remain sufficiently adherent to maintain a seal through the course of larval development, which often involves high humidity emanating from the wells that challenges adhesion. The Aeroseal Sealing Film is non-toxic to the animals, with a sufficiently small pore size, and remains sufficiently adherent to perform experiments reliably.

Assaying Methods

In one embodiment of the methods, a method for high throughput screening of compounds includes inducing a screenably distinct characteristic in wild-type *Drosophila* by feeding a high sugar diet to *Drosophila* embryos, feeding to the *Drosophila* embryos a compound that putatively modifies the screenably distinct characteristic, and screening the *Drosophila* to determine whether the compound modifies the screenably distinct characteristic. The high sugar diet has been shown to produce a wild type variant that manifests as developmental arrest of the *Drosophila* embryos, and ataxia in mature *Drosophila*. The developmental arrest and ataxia are both consistent with a glucose-mediated neuropathy in affected *Drosophila*, which is attributable to the toxicity of glucose at the high levels used in the growth medium. Either developmental arrest or ataxia function as screenably distinct characteristics that can be used as the basis for simple visual screening methods. The invention also encompasses any other simple screening methods which are based on the ability to easily discriminate an alteration in development behavior or gene expression in reaction to a high sugar, such as high glucose, environment.

The developmental arrest can be screened as described in the Examples, infra. Glucose, for example, induces readily observable delays in pupariation as determined by the timing of significant eclosion, and peak eclosion. For example, control *Drosophila* embryos show significant eclosion beginning at day 8, while *Drosophila* embryos exposed to high glucose growth medium show significant eclosion beginning at day 11 (1 molar glucose). Similarly, peak eclosion is delayed, for example, from day 10 in controls, to day 12 (1 molar glucose). Thus, candidate compounds are screened by observing changes to the delay in significant eclosion and peak eclosion, as compared to the developmental delay induced by high glucose.

The ataxia can be easily quantitated by negative geotaxis response. A suitable method for quantification is a simplified "one step" version of previous geotaxis "nine-step" assays, such as described in, e.g., McMillan, P. A. & McGuire, T. R., The homeotic gene spineless-aristapedia affects geotaxis in *Drosophila melanogaster*, *Behav. Genet* 22, 557-73 (1992); and Toma, D. P., White, K. P., Hirsch, J., & Greenspan, R. J., Identification of genes involved in *Drosophila melanogaster* geotaxis, a complex behavioral trait, *Nature Genetics* 31(4) 349-53 (2002), which are both herein incorporated by reference. In the current experimental paradigm, the geotaxis of *Drosophila* adults is assessed by tapping down flies to the bottom of the well and observing their ability to rapidly and smoothly climb to the top of the well. For animals that appear to have altered geotaxis, this simple and rapid preliminary test can be supplemented with the slower, more robust nine-step assay (McMillan, P. A. & McGuire, T. R. (1992)). Thus, candidate compounds are screened by observing changes in ataxia as measured by negative geotaxis response, as compared to the values obtained for negative geotaxis response under conditions of high sugar, such as high glucose.

Lethality of candidate compounds for *Drosophila* can be used to detect and quantify toxicity of candidate compounds. Well-known standard statistical methods are used to help distinguish chance results from real toxic effects. Lethality is quantified, for example, by determining the number of *Drosophila* that fail to develop successfully to adulthood and applying suitable statistical analyses to that number to determine statistical significance. For example, to determine the numbers of *Drosophila* that fail, given a fixed number of live embryos placed into each well, the embryos that successfully emerge as larvae are counted and this number subtracted from the total number of live embryos placed into the wells. Suitable statistical analyses are then applied to the number of failed embryos to determine its statistical significance. Lethal dose evaluations can be used to quantify the extent of toxicity. For example, once a candidate compound demonstrates a mediating effect on either ataxia or development delay induced by high glucose, the toxicity of the compound is evaluated by varying dosage levels across a broad range and quantifying the lethality of the compound at each dose to obtain an $LD_{50}$ value.

In another embodiment, there is provided a method of using wild-type *Drosophila* in a high throughput screening assay of compounds putatively modifying a screenably distinct characteristic in the wild-type *Drosophila*, the method comprising plating at least one wild-type *Drosophila* embryo in each of multiple wells in a multi-well microtiter plate, inducing tie screenably distinct characteristic in a plurality of the wild-type *Drosophila* embryos by feeding a high sugar diet to the *Drosophila* embryos, and screening the *Drosophila* to determine whether a candidate compound modifies the induced screenably distinct characteristic. In exemplary embodiments, the screenably distinct characteristic includes developmental arrest of *Drosophila*, or ataxia. Alternatively, the screenably distinct characteristic comprises an effect of neuropathy. The screenably distinct characteristic can also be an effect of glucose toxicity. In another embodiment, the method further includes screening the *Drosophila* to determine whether the compound has a toxic effect on the *Drosophila*.

In another embodiment, there is provided a method of preparing the wild-type *Drosophila* for use in a high throughput screening assay method, the method comprising feeding a high sugar diet to wild-type *Drosophila* embryos, thereby inducing a screenably distinct characteristic in the wild-type *Drosophila*. The screenably distinct characteristic is, for example, developmental arrest or ataxia.

Apparatus for Use in HTS Methods

In another aspect, the invention provides apparatus for use in high throughput screening methods as described herein. The apparatus includes a multi-well microtiter plate, an amount of a high sugar *Drosophila* growth medium placed into multiple wells of the multi-well microtiter plate, an amount of a candidate compound added to the multiple wells, and a plurality of screenably distinct wild-type *Drosophila* in the multiple wells, the screenably distinct *Drosophila* having developed from wild-type *Drosophila* embryos fed the high sugar growth medium. The screenably distinct *Drosophila* include, for example, developmentally arrested *Drosophila* embryos, or ataxic *Drosophila*. In one embodiment, the apparatus further includes a sealing film for sealing each well of the multi-well microtiter plate. The sealing film is, for example, Aeroseal sealing film.

Automated Screening

Preparation of the microtiter plates with the growth medium, *Drosophila* embryos and candidate compounds can be performed manually or using a robotic system or systems. For example, plating of the growth medium and of candidate compounds in solution on the microtiter plates can be readily adapted to known robotic systems that can be configured to repeatedly inject a predetermined volume of the growth medium and of the test solutions into each well of the microtiter plate. Similarly, the assay results can be determined manually, or can be adapted to automated or robotic analyzers.

Kits

Further, the present invention provides a kit for use in a method for high throughput screening of compounds. The kit includes, for example, apparatus for use in high throughput screening as described supra, together with instructions for using the kit. For example, in one embodiment the kit contain instructions for the following: for inducing a screenably distinct characteristic in wild-type *Drosophila* by feeding a high sugar diet to the wild-type *Drosophila* embryos, instructions for feeding to the *Drosophila* embryos a compound that putatively modifies the screenably distinct characteristic, and instructions for screening the *Drosophila* to determine whether the compound modifies the screenably distinct characteristic. In one embodiment, the instructions set forth more specifically instructions for inducing developmental arrest of *Drosophila* embryos, or for inducing ataxia in mature *Drosophila*. In another embodiment, the instructions set forth more specifically instructions for inducing neuropathy in the *Drosophila*. In another embodiment, the instructions set forth more specifically instructions for screening the *Drosophila* to determine whether the compound modifies glucose-mediated toxicity in the *Drosophila*. In still another embodiment, the instructions set forth instructions for determining whether the compound has a toxic effect on the *Drosophila*. In yet another embodiment, the kit further includes a multi-well microtiter plate, and an amount of a high sugar *Drosophila* growth medium for placement into multiple wells of the multi-well microtiter plate. The kit can still further include the sealing film for sealing each well of the multi-well microtiter plate, and an exemplary sealing film is the Aeraseal sealing film.

Other Embodiments

The invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In particular, the examples infra demonstrate the usefulness of the methods and related articles of composition with respect to screening for compounds affecting glucose-mediated diseases and conditions such as diabetes, diabetic nephropathy and diabetic neuropathy including retinopathy, glucose toxicity and metabolic syndrome. However, also contemplated is the applicability of the *Drosophila* screening model to other diseases and conditions besides diabetes and related glucose-mediated diseases and conditions. For example, the *Drosophila* screening model can also be used to screen for compounds that modify how organisms respond to more general environmental stresses that have been implicated in cellular degeneration diseases such as Alzheimer's Disease and Parkinson's Disease, as well as processes leading to aging. In particular, given the now recognized implication of cellular free radical compounds in the genesis of cellular degenerative processes, it is believed that delivery of compounds that increase cellular free-radicals will likely result in neuronal damage that will mimic any number of screenably distinct neuropathological syndromes.

In addition, several proposed mechanisms for diabetic neuropathy in humans and in mammalian model systems invoke neuronal damage mediated by an accumulation of advanced glycosylation end products, and osmotic-mediated damage secondary to metabolic byproducts of glucose. Brownlee, M., Biochemistry and molecular cell biology of diabetic complications, *Nature* 414(6865): 813-20 (2001); Yasuda, H., M. Terada, et al., Diabetic neuropathy and nerve regeneration, *Prog. Neurobiol.* 69(4): 229-85 (2001), which are both herein incorporated by reference. The glucose toxicity model of ataxia/neuropathy as described herein will be a useful system for identifying factors that either enhance or suppress the neuropathy, and the ataxia. Genetic approaches can be utilized to identify the pathways acted on by candidate compounds to alleviate the observed ataxia.

The following experimental examples describing screening of exemplary candidate compounds are offered by way of illustration and not by way of limitation.

EXAMPLE 1

The small molecule glyburide was tested using the *Drosophila* screening method and related articles of composition, and assessed according to its ability to affect the developmental delay induced by glucose in developing *Drosophila* larvae. Glyburide, and nateglinide (see Example 2) were chosen because they are orally absorbed compounds that are currently used to treat patients with diabetes.

Using the high throughput screening method, glyburide demonstrated an ability to ameliorate glucose-mediated developmental delay and accordingly has been identified as a candidate lead compound for further testing and development as a therapeutic compound for treatment of diabetes and other disease attributable to the toxic effect of high glucose conditions, including neuropathy and retinopathy.

Figure 2:
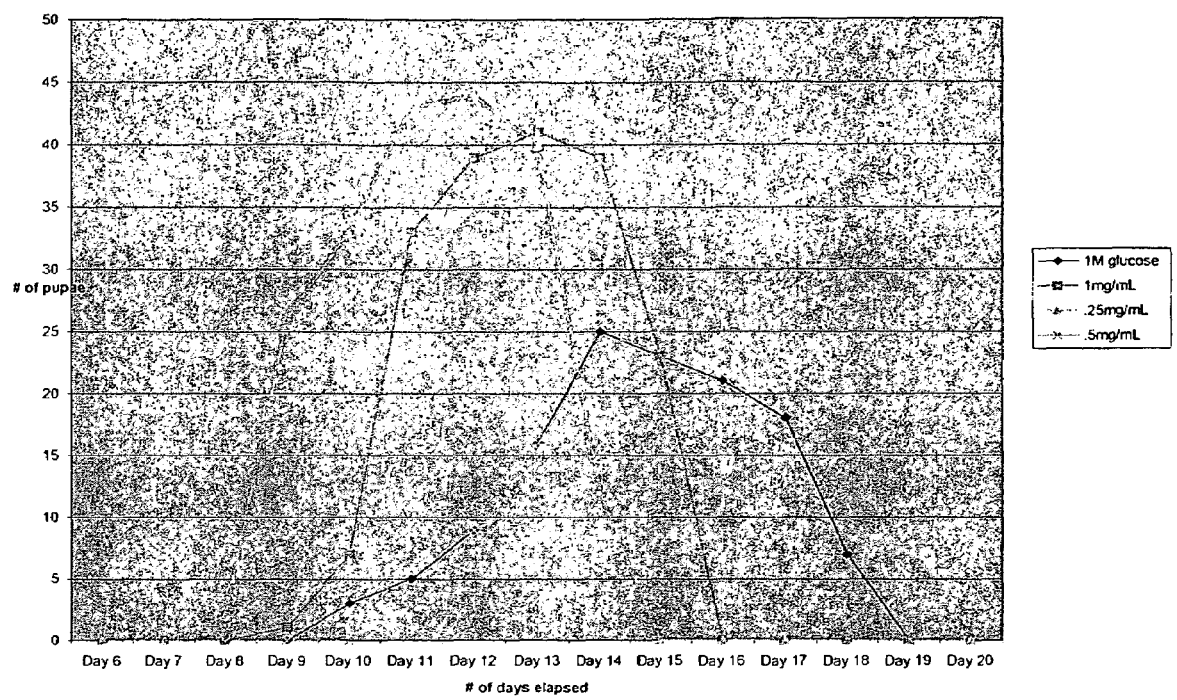
FIG. 2 is a graph showing the effect of the small molecule glyburide on glucose-mediated delay in pupariation.

FIG. 2 demonstrates the effect of glyburide. In the presence of high glucose (1 M glucose in otherwise standard *Drosophila* growth media), glyburide reduced glucose-mediated delay in pupariation. Control animals (no drug, 1 M glucose) showed significant levels of pupariation at approximately day 12 and high levels at day 13-14. Addition of glyburide (0.25 mg and 1 mg per ml of *Drosophila* growth media) in the presence of high glucose reduced the glucose-mediated delay: at 0.25 mg/ml, experimental animals showed significant levels of pupariation at day 8 and high levels by day 10; animals that received 1 mg/ml glyburide began both significant and high levels of pupariation at day 11.

EXAMPLE 2

The small molecule nateglinide was tested using the *Drosophila* screening method and related articles of composition, and assessed according to its ability to affect the developmental delay induced by glucose in developing *Drosophila* larvae.

Using the high throughput screening method, nateglinide demonstrated an ability to ameliorate glucose-mediated developmental delay and accordingly has been identified as a candidate lead compound for further testing and development as a therapeutic compound for treatment of diabetes and other disease attributable to the toxic effect of high glucose conditions, including neuropathy and retinopathy.

Figure 3:
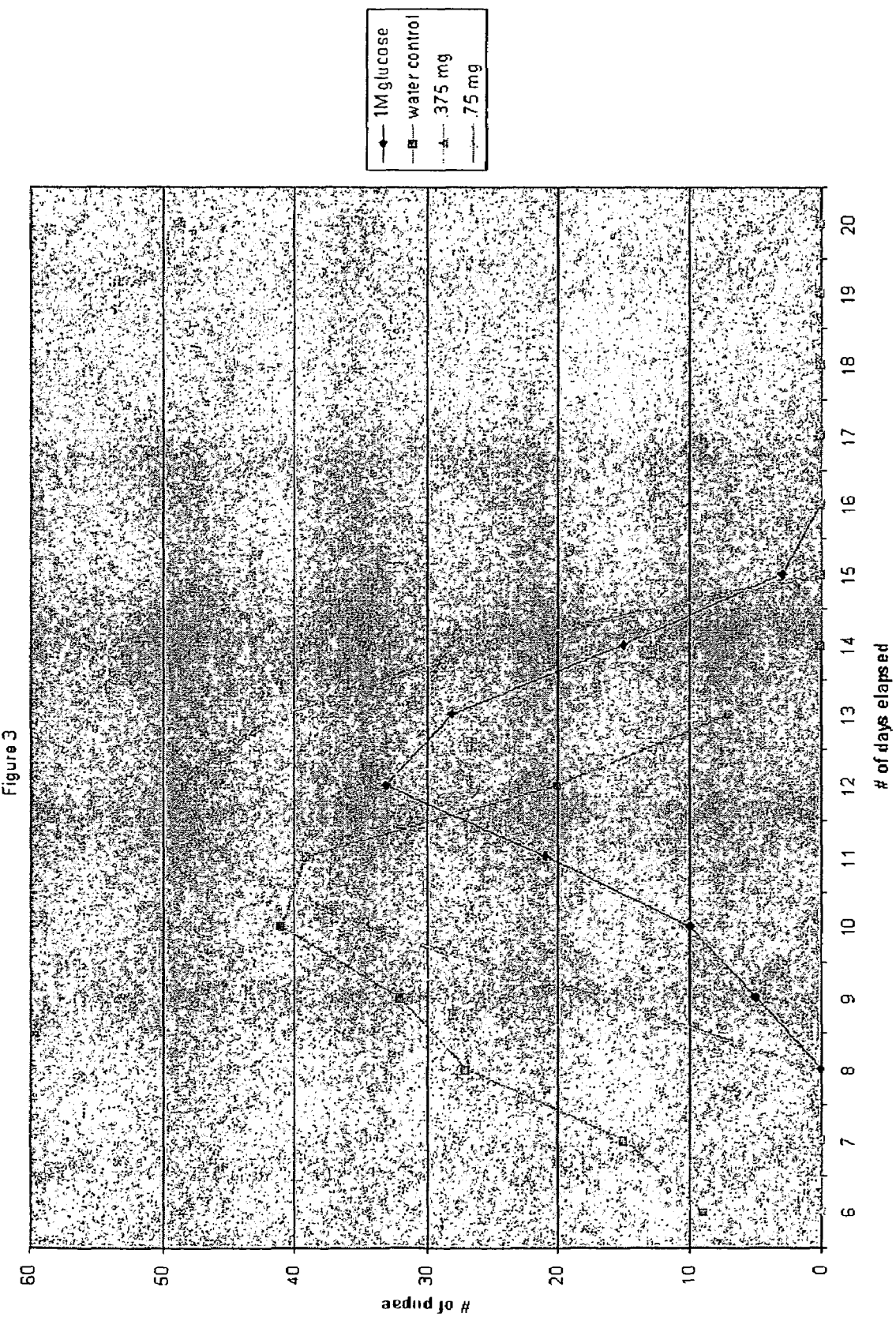
FIG. 3 is a graph showing the effect of the small molecule nateglinide on glucose-mediated delay in pupariation.

FIG. 3 demonstrates the effect of nateglinide. High glucose delays pupariaton from significant eclosion beginning at day 8 (water control) to significant eclosion beginning at day 11 (1 molar glucose); peak eclosion was also delayed from day 10 (water control) to day 12 (1 molar glucose). Nateglinide (0.375 mg/ml of food) partially restored the rate of development, with pupariation showing high rates beginning at day 9 and achieving a peak between days 10 and 11. The higher (0.75 mg/ml of food) levels of nateglinide gave an intermediate result, with high levels beginning at day 9 and peaking between days 11 and 12.

EXAMPLE 3

Hexose products of glucose metabolism are thought to have roles as mediators of toxicity associated with high levels of glucose. Fructose, sorbitol, galactose, and glucosamine have previously been implicated as intermediates responsible for various aspects of diabetic complications (Chung S S, Ho E C, Lam K S, Chung S K, Contribution of polyol pathway to diabetes-induced oxidative stress, *J. Am. Soc. Nephrol.* (8 Suppl 3):S233-6 August 14 (2003); Evans J L, Goldfine I D, Maddux B A, Grodsky G M, Oxidative stress and stress-activated signaling pathways: a unifying hypothesis of type 2 diabetes, *Endocr. Rev.* 23(5):599-622 (2002); Tomlinson D R, Stevens E J, Diemel L T, Aldose reductase inhibitors and their potential for the treatment of diabetic complications, *Trends Pharmacol Sci.* 15(8):293-7 (1994); Rumberger J M, Wu T, Hering M A, Marshall S., Role of hexosamine biosynthesis in glucose-mediated up-regulation of lipogenic enzyme mRNA levels: effects of glucose, glutamine, and glucosamine on glycerophosphate dehydrogenase, fatty acid synthase, and acetyl-CoA carboxylase mRNA levels, *J. Biol. Chem.* 2003 Aug. 1, 278(31):28547-52.; Wells L, Hart G W, O-GlcNAc turns twenty: functional implications for post-translational modification of nuclear and cytosolic proteins with a sugar, *FEBS Lett.* 2003 Jul. 3;546(1):154-8; Wells L, Vosseller K, Hart G W, A role for N-acetylglucosamine as a nutrient sensor and mediator of insulin resistance, *Cell Mol Life Sci.* 2003 February; 60(2):222-8).

Figure 4:
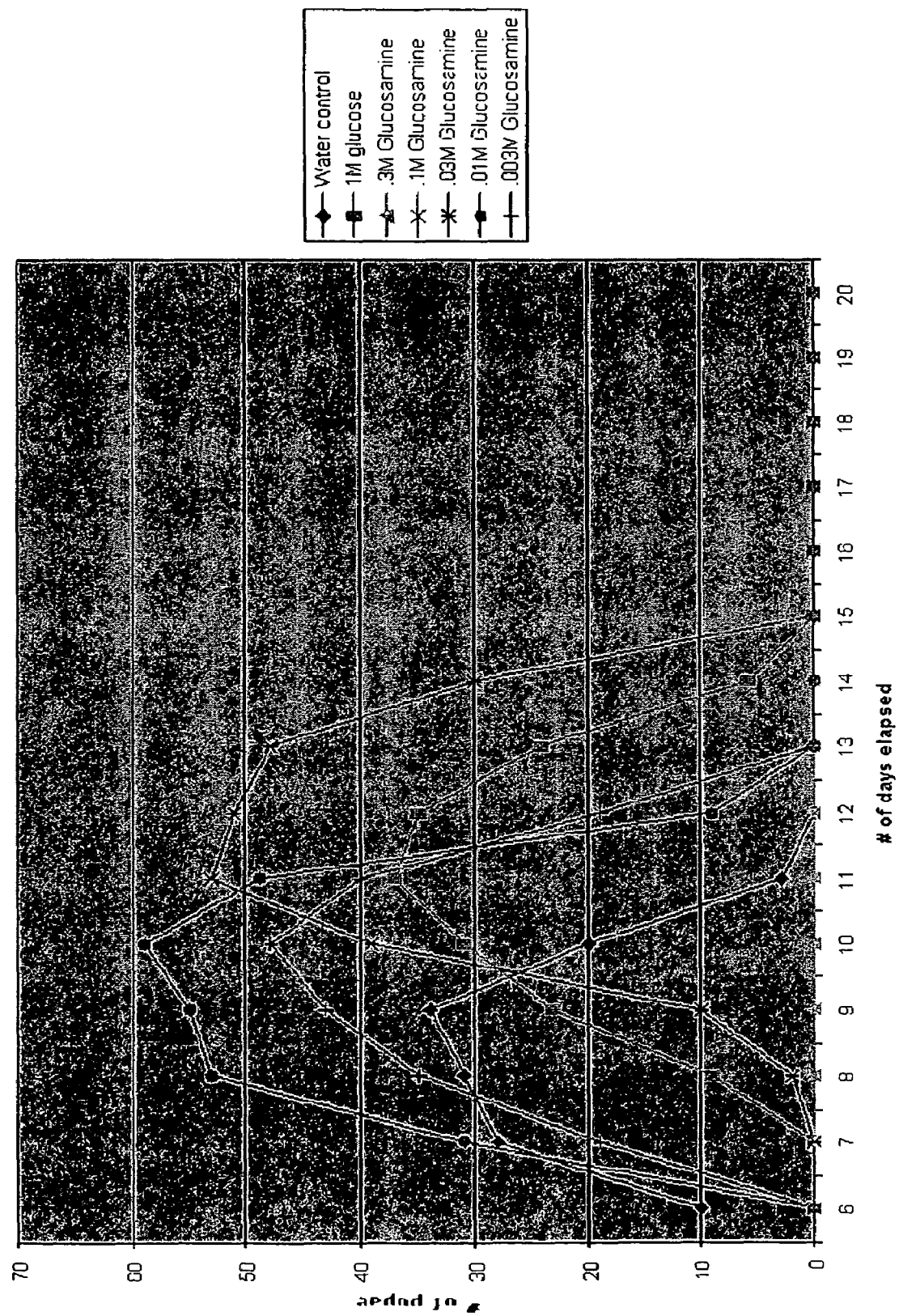
FIG. 4 is a graph showing the delaying effects on pupariation of growth media containing high amounts of glucosamine.

Accordingly, the ability of the hexose sugars fructose, sorbitol, galactose and glucosamine was tested by adding amounts of each sugar to the standard *Drosophila* growth medium. Fructose and sorbitol induced a 48-hour developmental delay at concentrations similar to those at which glucose induced developmental delay (data not shown). Galactose demonstrates toxicity at 0.3 M (data not shown), as compared to about 1.0 M for glucose. FIG. 4 shows the effects of glucosamine. Glucosamine is still more potent than galactose, inducing a developmental delay at concentrations as low as 3 mM in the *Drosophila* growth media. Progressively higher levels of glucosamine lead to progressively longer developmental delays compared to water-added controls. At highest levels of glucosamine (0.1 M and 0.3 M), most larvae failed to emerge.

These data show that hexose products of glucose can act as mediators of the development delay in *Drosophila* that is associated with high levels of glucose. These results therefore support the application of the *Drosophila* screening method to the identification of candidate compounds, other drugs or genes that might ameliorate toxicity mediated by hexose sugars in addition to glucose.

REFERENCES CITED

All references cited above are incorporated herein by reference in their entirety and for all purposes to the same extent as if each individual publication, patent or patent application was specifically and individually indicated to be incorporated by reference in its entirety for all purposes. Citation of a reference herein shall not be construed as an admission that such is prior art to the present invention.

What is claimed is:

1. A method for high throughput screening of compounds comprising:
    inducing a screenably distinct characteristic in wild-type *Drosophila* by feeding a diet high in a sugar comprising a hexose product of glucose metabolism to *Drosophila* larvae,
    feeding to the *Drosophila* larvae a compound that putatively modifies the screenably distinct characteristic; and
    screening the *Drosophila* to determine whether the compound modifies the screenably distinct characteristic; wherein
        the screenably distinct characteristic comprises developmental arrest or ataxia; and
        the level of the sugar comprising a hexose product of glucose metabolism is sufficient to prolong larval development by greater than or equal to 48 hours relative to a larvae grown on standard medium.

2. A method according to claim 1 wherein the sugar comprising a hexose product of glucose metabolism is selected from the group consisting of glucose, fructose, sorbitol, galactose, glucosamine, sucrose, maltose, and lactose.

3. A method according to claim 1 wherein the sugar comprising a hexose product of glucose metabolism is glucose.

4. A method according to claim 1 wherein the screenably distinct characteristic comprises developmental arrest.

5. A method according to claim 1 wherein the screenably distinct characteristic comprises ataxia.

6. A method according to claim 1 further comprising screening the *Drosophila* to determine whether the compound has a toxic effect on the *Drosophila*.

7. A method of using wild-type *Drosophila* in a high throughput screening assay of compounds putatively modifying a screenably distinct characteristic in the wild-type *Drosophila*, said method comprising:
    plating at least one wild-type *Drosophila* embryo in each of multiple wells in a multi-well microtiter plate;
    adding a compound that putatively modifies a screenably distinct characteristic in *Drosophila* to the multiple wells;
    inducing the screenably distinct characteristic in a plurality of the wild-type *Drosophila* embryos by feeding a diet high in amount of a sugar comprising a hexose product of glucose metabolism to the *Drosophila* embryos;
    screening the *Drosophila* to determine whether a candidate compound modifies the induced screenably distinct characteristic; wherein
        the screenably distinct characteristic comprises developmental arrest or ataxia; and
        the level of the sugar comprising a hexose product of glucose metabolism is sufficient to prolong larval development by greater than or equal to 48 hours relative to a larvae grown on standard medium.

8. A method according to claim 7 wherein the sugar comprising a hexose product of glucose metabolism is selected from the group consisting of glucose, fructose, sorbitol, galactose, glucosamine, sucrose, maltose, and lactose.

9. A method according to claim 7 wherein the sugar comprising a hexose product of glucose metabolism is glucose.

10. A method according to claim 7 wherein the screenably distinct characteristic comprises developmental arrest.

11. A method according to claim 7 wherein the screenably distinct characteristic comprises ataxia.

12. A method according to claim 7 further comprising determining whether the compound has a toxic effect on the *Drosophila*.

13. A method of preparing wild-type *Drosophila* for use in a high throughput screening assay method, said method comprising
feeding a diet high in an amount of a sugar comprising a hexose product of glucose metabolism to wild-type *Drosophila* embryos thereby inducing a screenably distinct characteristic in the wild-type *Drosophila*; wherein
the screenably distinct characteristic comprises developmental arrest or ataxia; and
the level of the sugar comprising a hexose product of glucose metabolism is sufficient to prolong larval development by greater than or equal to 48 hours relative to a larvae grown on standard medium.

14. A method according to claim 13 wherein the sugar comprising a hexose product of glucose metabolism is selected from the group consisting of glucose, fructose, sorbitol, galactose, glucosamine, sucrose, maltose, and lactose.

15. A method according to claim 13 wherein the sugar comprising a hexose product of glucose metabolism is glucose.

16. A method according to claim 13 wherein the screenably distinct characteristic comprises developmental arrest.

17. A method according to claim 13 wherein the screenably distinct characteristic comprises ataxia.

18. A method according to claim 1 wherein the sugar comprising a hexose product of glucose metabolism is selected from the group consisting of glucose, fructose, sorbitol, galactose, glucosamine, maltose, and lactose.

19. A method according to claim 1 wherein the sugar comprising a hexose product of glucose metabolism is selected from the group consisting of glucose, fructose, sorbitol, galactose, and glucosamine.

20. A method according to claim 7 wherein the sugar comprising a hexose product of glucose metabolism is selected from the group consisting of glucose, fructose, sorbitol, galactose, glucosamine, maltose, and lactose.

21. A method according to claim 7 wherein the sugar comprising a hexose product of glucose metabolism is selected from the group consisting of glucose, fructose, sorbitol, galactose, and glucosamine.

22. A method according to claim 13 wherein the sugar comprising a hexose product of glucose metabolism is selected from the group consisting of glucose, fructose, sorbitol, galactose, glucosamine, maltose, and lactose.

23. A method according to claim 13 wherein the sugar comprising a hexose product of glucose metabolism is selected from the group consisting of glucose, fructose, sorbitol, galactose, and glucosamine.

* * * * *

UNITED STATES PATENT AND TRADEMARK OFFICE
CERTIFICATE OF CORRECTION

| | | |
|---|---|---|
| PATENT NO. | : 7,642,066 B2 | Page 1 of 1 |
| APPLICATION NO. | : 11/036897 | |
| DATED | : January 5, 2010 | |
| INVENTOR(S) | : Baranski et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 488 days.

Signed and Sealed this

Sixteenth Day of November, 2010

David J. Kappos
*Director of the United States Patent and Trademark Office*